United States Patent [19]
Sudoh et al.

[11] 4,344,062
[45] Aug. 10, 1982

[54] HUMIDITY SENSOR ELEMENT

[75] Inventors: Giichi Sudoh, Chichibu; Keiichi Minegishi, Kumagaya; Tokuji Akiba, Kumagaya; Tadao Kato, Kumagaya; Norio Ogawa, Kumagaya, all of Japan

[73] Assignee: Chichibu Cement Co., Ltd., Japan

[21] Appl. No.: 156,192

[22] Filed: Jun. 3, 1980

[30] Foreign Application Priority Data

Jun. 7, 1979 [JP] Japan .................................. 54-70608

[51] Int. Cl.³ .............................................. H01L 7/00
[52] U.S. Cl. ...................................... 338/35; 252/520
[58] Field of Search ............. 338/35; 73/27 R, 336.5; 422/98; 252/520, 518; 29/610; 264/61

[56] References Cited

U.S. PATENT DOCUMENTS

| | | | |
|---|---|---|---|
| 3,721,631 | 3/1973 | Sumi et al. | 338/35 X |
| 3,748,625 | 7/1973 | Bennewitz | 338/35 X |
| 4,015,230 | 3/1977 | Nitta et al. | 338/35 |

*Primary Examiner*—C. L. Albritton
*Attorney, Agent, or Firm*—Wenderoth, Lind & Ponack

[57] ABSTRACT

A humidity sensor element comprising a metal oxide semiconductor sintered member having a composition composed of $TiO_2$ and $V_2O_5$, the member being formed with a pair of electrodes. When the element is used at a temperature of less than 400° C., it is possible to detect the humidity as a variation of electric resistance.

2 Claims, 5 Drawing Figures

HUMIDITY SENSOR ELEMENT

BACKGROUND OF THE INVENTION

1. Field of the Invention

This invention relates to a humidity sensor element for detecting a humidity as a variation of electric resistance.

2. Description of the Prior Art

Generally, a certain kind of metal oxide semiconductor has a good water absorbing property and it is known that molecules of water are absorbed into and removed from the metal oxide semiconductor whereby the resistance value of the metal oxide semiconductor varies.

The abovementioned properties can be utilized to make a humidity sensor element. However, conventional humidity sensor elements have disadvantages that the reproductivity is poor, change in lapse of time is great, sensitive speed is slow, and volume resistivity by which detection can be made electrically with high accuracy is not provided.

OBJECT

It is an object of this invention to provide a humidity sensor element having various features in which the change in resistance to change in humidity is large, the reproductivity thereof is good, no change in lapse of time of resistance value involves, the device is extremely stable, and the sensitive speed is very quick.

It is a further object of the invention to provide a humidity sensor element which has a good durability and which can be provided at extremely low cost.

DETAILED DESCRIPTION OF THE INVENTION

Figure 1:
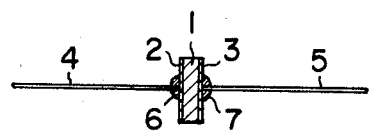
FIG. 1 is a sectional view of one embodiment in accordance with the present invention.

FIG. 1 shows a construction of a preferred embodiment of the present invention, the device being manufactured in the following procedure.

First, 0.1 to 10 mole percentage of $V_2O_5$ is added to $TiO_2$ as a principal material, which are completely crushed and mixed, after which it is presintered preferably at a temperature of from 600° C. to 800° C., then the material is subjected to press molding at a pressure of 500 kg/cm$^2$, and the thus molded material is finally sintered at a temperature of from 900° C. to 1,300° C. for five hours to form a disk-shaped sintered member of thickness 4 mm and diameter 10 mm.

Next, silver paste is baked onto the opposite surfaces of the disk-shaped sintered member 1 to form a pair of electrodes 2 and 3 to which lead wires 4 and 5 are bonded by a solder 6.

It is necessary to select a ratio of composition between $TiO_2$ and $V_2O_5$ which constitute a disk-shaped sintered member 1 to a value less than 10 mole %.

The reason therefor is that if the ratio of composition of $V_2O_5$ exceeds 10 mole %, the resistance value of the element becomes high similarly to the case where $V_2O_5$ is not added, rendering it unpractical. If the ratio of composition of $V_2O_5$ is selected to a value less than 10 mole %, the resistance value lowers to the practical range.

This will be described in view of test results.

The ratio of composition between TiO and $V_2O_5$ as specimen used in the test will be given in Table 1 below.

TABLE 1

| SPECIMEN | Ratio of composition (Mole %) COMPOSITION | |
|---|---|---|
| | $TiO_2$ | $V_2O_5$ |
| 1 | 100.0 | 0.0 |
| 2 | 98.0 | 2.0 |
| 3 | 96.0 | 4.0 |
| 4 | 94.0 | 6.0 |
| 5 | 85.0 | 15.0 |

Figure 2:
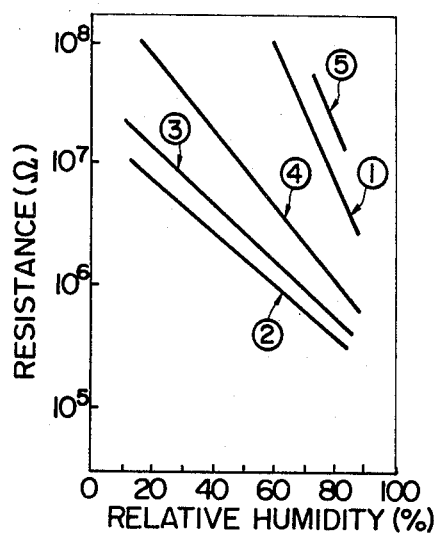
FIG. 2 is a view showing the relation between the relative humidity and the resistance value of the humidity sensor element in accordance with the present invention.

With respect to the humidity sensor element in which the dish-shaped sintered member 1 composed of each of the aforesaid ratio of composition is provided with electrodes 2, 3 and lead wires 4, 5, the relation between the relative humidity and the resistance value obtained is as follows. The measured results are as shown in FIG. 2. The values of reference numerals in FIG. 2 correspond to those numerals of specimen used in Table 1.

It is apparent from FIG. 2 that when the relative humidity is varied from 0% to 100%, the resistance value of the specimen 2, 3 and 4 linearly varies from $2 \times 10^8 \Omega$ to $2 \times 10^5 \Omega$. It is evident that since specimen 1 and 5 outside the range defined in the present invention have high resistance, the measurement in the region of low humidity is difficult and not practical. It will be noted that in this reaction, no hysteresis appears, exhibiting the stabilized characteristic.

Figure 3:
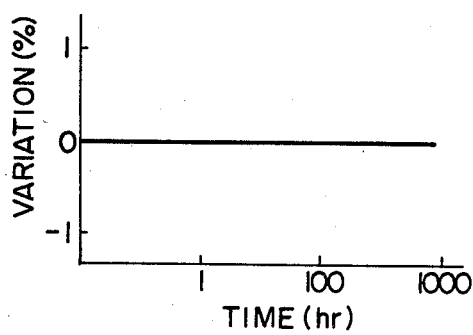
FIG. 3 is a view showing the characteristic of lapse of time of the humidity sensor element in accordance with the present invention.

Next, the specimen 2 is left as it is for 100 hours under the relative humidity 90% at 25° C. in order to examine the change in lapse of time of resistance value. The measured results are given in FIG. 3. It will be apparent from FIG. 3 that no change in lapse of time of resistance value is made, exhibiting the stabilized characteristic.

Figure 4:
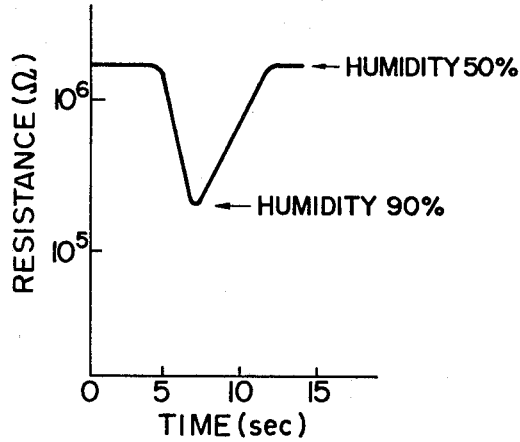
FIG. 4 is a view showing the characteristic of sensitive speed of the humidity sensor element in accordance with the present invention.

Further, the sensitive speed (resistance value - time) of the specimen 2 was observed with the relative humidity varied from 50% to 90%. The measured results are given in FIG. 4. As may be seen from FIG. 4, it takes several seconds to reach the equilibrium, which is high speed enough to serve for practical use. Particularly, the responsiveness of change from high to low humidity does away with the conventional conception.

As described above, the humidity sensor element in accordance with the present invention has various features that the change in resistance to change in humidity is large, the reproductivity thereof is good, no change in lapse of time of resistance value involves, the device is extremely stable, and the sensitive speed is very quick. In addition, since the humidity sensor element of the present invention is a sintered member, it has good durability and can be manufactured at very low cost. While a DC power source has been used in the abovementioned embodiment for measurement, it is possible to use an AC power source to achieve a similar effect.

The humidity sensor element in accordance with the present invention as previously described in detail has good characteristics that may not be achieved by prior arts, has high practical values and can be greatly contributed to the fields of measurement and control.

The using condition of the humidity sensor element in accordance with the present invention is that it has to be used at a temperature below 400° C., preferably, at a temperature in the vicinity of room temperature. Because, if the temperature of the humidity sensor element exceeds 400° C., the width of variation in resistance value to the humidity becomes small, which is not suitable for practical use.

Figure 5:
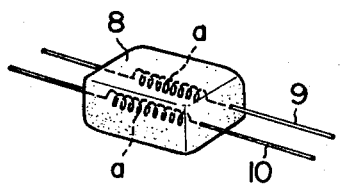
FIG. 5 is a perspective view of a different mode of embodiment in accordance with the present invention.

FIG. 5 shows an embodiment of the present invention which is of the volume production type.

Instead of employing the form provided with the electrodes 2 and 3 as in the embodiment shown in FIG. 1, the humidity sensor element of FIG. 5 comprises a granular sintered member 8 having its size 5 mm×3 mm×2 mm, into which is embedded and connected lead wires 9 and 10 of 0.05 mm spaced 1 mm apart formed in the central portion thereof with coiled electrode portions a of outer diameter 0.7 mm. The number of windings of the coiled electrode portion a is 20.

In this humidity sensor element, for example, $TiO_2$ and $V_2O_5$ are selected so as to have the ratio of composition as shown in the abovementioned Table 1, the $TiO_2$ and $V_2O_5$ are completely crushed and mixed, after which it is presintered at 600° C. for five hours, then the thus sintered material is introduced into a mold together with lead wires 9 and 10 for press molding at a pressure of 100 kg/cm², and it is heated and sintered at a temperature of 900° to 1,300° C. for five hours to obtain a granular sintered member 8 with coiled electrode portions a of the lead wires 9 and 10 embedded therein, that is, to obtain a humidity sensor element.

While an arrangement wherein the coiled electrodes are incorporated in the lead wires as described above has been employed also in another sensor elements, it offers various advantages that since soldering operation for the lead wires is not required, the device can be provided at low cost; the lead wires are prevented from being slipped out; and the surface area of electrodes may be obtained, thus such an arrangement being excellent in application to a construction of a volume production type sensor element.

I claim:

1. A humidity sensor element comprising a metal oxide semiconductor sintered member composed of a composition of $TiO_2$ as a principal material and containing 0.1 to 10 mole % of $V_2O_5$, said member being provided with electrodes.

2. A humidity sensor element according to claim 1, wherein the metal oxide semiconductor sintered member is in the form of a disk, and silver paste is baked onto the opposite surfaces of the sintered member to form a pair of electrodes, each of said electrodes having a lead wire soldered thereon.

* * * * *